(12) United States Patent
Sheu et al.

(10) Patent No.: US 11,085,134 B2
(45) Date of Patent: Aug. 10, 2021

(54) FABRIC-BASED USER INTERFACE BUTTONS AND DEFORMABLE USER INTERFACE USING BI-ELASTIC FORMED INFORMATION HANDLING SYSTEM CHASSIS

(71) Applicant: Dell Products L.P., Round Rock, TX (US)

(72) Inventors: Weijong Sheu, Austin, TX (US); Deeder M. Aurongzeb, Austin, TX (US); Christopher A. Torres, San Marcos, TX (US)

(73) Assignee: Dell Products L.P., Round Rock, TX (US)

( * ) Notice: Subject to any disclaimer, the term of this patent is extended or adjusted under 35 U.S.C. 154(b) by 0 days.

(21) Appl. No.: 16/737,678

(22) Filed: Jan. 8, 2020

(65) Prior Publication Data

US 2021/0207297 A1    Jul. 8, 2021

(51) Int. Cl.
    *G01L 1/18*    (2006.01)
    *D03D 1/00*    (2006.01)
    *A61B 5/00*    (2006.01)

(52) U.S. Cl.
CPC ......... *D03D 1/0088* (2013.01); *A61B 5/6804* (2013.01); *G01L 1/18* (2013.01); *D10B 2401/16* (2013.01); *D10B 2403/02431* (2013.01)

(58) Field of Classification Search
CPC ...... G06F 3/0416; G06F 3/0443; G06F 3/016; G06F 2203/04107; G06F 2203/04102; G06F 1/163; H03K 2017/9602; H03K 2217/94094
See application file for complete search history.

(56) References Cited

U.S. PATENT DOCUMENTS

| 10,072,998 | B2 * | 9/2018 | Chang ................... G01L 9/0072 |
| 2014/0373594 | A1 * | 12/2014 | Remez ................... G01L 1/146 |
| | | | 73/1.08 |
| 2017/0234673 | A1 * | 8/2017 | Sibbett ................... G01L 1/205 |
| | | | 73/777 |

OTHER PUBLICATIONS

Definition of "Piezoelectric Effect", The New IEEE Standard Dictionary of Electrical Electronics Terms, Fifth Ed. (1993).

* cited by examiner

*Primary Examiner* — Brandi N Hopkins
(74) *Attorney, Agent, or Firm* — Jackson Walker L.L.P.

(57) ABSTRACT

A fabric cover may be configured to mechanically couple to and cover part of a frame and the fabric cover may have a plurality of layers including a first non-conductive fabric layer, a second non-conductive fabric layer, a piezoresistive core layer between the first non-conductive fabric layer and the second fabric non-conductive layer, and a first conductive layer comprising a plurality of first conductive fiber traces and located between the first non-conductive fabric layer and the second non-conductive fabric layer. A localized impedance of the piezoresistive core layer indicates a mechanical force applied to the fabric cover proximate to such localized impedance.

19 Claims, 7 Drawing Sheets

FABRIC-BASED USER INTERFACE BUTTONS AND DEFORMABLE USER INTERFACE USING BI-ELASTIC FORMED INFORMATION HANDLING SYSTEM CHASSIS

TECHNICAL FIELD

The present disclosure relates in general to information handling systems, and more particularly to systems and methods for implementing user interface buttons and a deformable user interface using a bi-elastic formed information handling system chassis.

BACKGROUND

As the value and use of information continues to increase, individuals and businesses seek additional ways to process and store information. One option available to users is information handling systems. An information handling system generally processes, compiles, stores, and/or communicates information or data for business, personal, or other purposes thereby allowing users to take advantage of the value of the information. Because technology and information handling needs and requirements vary between different users or applications, information handling systems may also vary regarding what information is handled, how the information is handled, how much information is processed, stored, or communicated, and how quickly and efficiently the information may be processed, stored, or communicated. The variations in information handling systems allow for information handling systems to be general or configured for a specific user or specific use such as financial transaction processing, airline reservations, enterprise data storage, or global communications. In addition, information handling systems may include a variety of hardware and software components that may be configured to process, store, and communicate information and may include one or more computer systems, data storage systems, and networking systems.

Because of their mobility, consumers of information handling systems increasingly use laptops. A laptop, often referred to as a "notebook", may be a small, portable information handling system with a "clamshell" form factor including a keyboard assembly on a lower portion of the clamshell and a display assembly comprising a thin liquid crystal display screen or light-emitting diode display screen on an upper portion of the clamshell, with the keyboard assembly mechanically coupled to the display assembly via a mechanical hinge. Accordingly, the keyboard assembly and the display assembly may be rotated to an open position in order for a user to use the laptop. Conversely, a user may fold a laptop into its closed position for transportation, and thus may be suitable for mobile use.

In addition to functionality, users of information handling systems may also choose an information handling system based on aesthetic appearance. For example, customers of notebook information handling systems often desire thin and sleek form factors. In addition, manufacturers of notebook information handling systems are developing notebook information handling systems having an enclosure constructed with foldable textile-like fiber, providing an appearance of a book bound in fabric, which may be desirable to some users.

However, by transitioning information handling systems from plastic and metal exteriors to fabric exteriors, mechanical buttons present on information handling systems with plastic and metal exteriors may not readily be formed on a fabric exterior using known techniques.

SUMMARY

In accordance with the teachings of the present disclosure, the disadvantages and problems associated with existing approaches to implementing user interface buttons and a deformable user interface using a bi-elastic formed information handling system chassis may be reduced or eliminated.

In accordance with embodiments of the present disclosure, a system may include a frame, a fabric cover mechanically coupled to and covering part of the frame, the fabric cover comprising a plurality of layers including a first non-conductive fabric layer, a second non-conductive fabric layer, a piezoresistive core layer between the first non-conductive fabric layer and the second non-conductive fabric layer, and a first conductive layer comprising a plurality of first conductive fiber traces and located between the first non-conductive fabric layer and the second non-conductive fabric layer. The system may also include a first contact assembly mechanically coupled to the frame and comprising a plurality of first electrical contacts, each of the first electrical contacts electrically coupled to a corresponding one of the plurality of first conductive fiber traces and a processing subsystem communicatively coupled to the first contact assembly and configured to determine a location of the fabric cover in which a localized impedance of the piezoresistive core layer indicates a mechanical force applied to the fabric cover proximate to such localized impedance.

In accordance with these and other embodiments of the present disclosure, a fabric cover may be configured to mechanically couple to and cover part of a frame and the fabric cover may have a plurality of layers including a first non-conductive fabric layer, a second non-conductive fabric layer, a piezoresistive core layer between the first non-conductive fabric layer and the second fabric non-conductive layer, and a first conductive layer comprising a plurality of first conductive fiber traces and located between the first non-conductive fabric layer and the second non-conductive fabric layer. A localized impedance of the piezoresistive core layer indicates a mechanical force applied to the fabric cover proximate to such localized impedance.

In accordance with these and other embodiments of the present disclosure, a method may include coupling a fabric cover to a frame to cover the frame, the fabric cover comprising a plurality of layers including a first non-conductive fabric layer, a second non-conductive fabric layer, a piezoresistive core layer between the first non-conductive fabric layer and the second non-conductive fabric layer, and a first conductive layer comprising a plurality of first conductive fiber traces and located between the first non-conductive fabric layer and the second non-conductive fabric layer. The method may also include mechanically coupling a first contact assembly mechanically to the frame, the first contact assembly comprising a plurality of first electrical contacts, each of the first electrical contacts electrically coupled to a corresponding one of the plurality of first conductive fiber traces. The method may further include communicatively coupling a processing subsystem to the first contact assembly, the processing subsystem configured to determine a location of the fabric cover in which a localized impedance of the piezoresistive core layer indicates a mechanical force applied to the fabric cover proximate to such localized impedance.

Technical advantages of the present disclosure may be readily apparent to one skilled in the art from the figures, description and claims included herein. The objects and advantages of the embodiments will be realized and achieved at least by the elements, features, and combinations particularly pointed out in the claims.

It is to be understood that both the foregoing general description and the following detailed description are examples and explanatory and are not restrictive of the claims set forth in this disclosure.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION

Preferred embodiments and their advantages are best understood by reference to FIGS. 1 through 8, wherein like numbers are used to indicate like and corresponding parts.

For the purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, entertainment, or other purposes. For example, an information handling system may be a personal computer, a personal digital assistant (PDA), a consumer electronic device, a network storage device, or any other suitable device and may vary in size, shape, performance, functionality, and price. The information handling system may include memory, one or more processing resources such as a central processing unit ("CPU") or hardware or software control logic. Additional components of the information handling system may include one or more storage devices, one or more communications ports for communicating with external devices as well as various input/output ("I/O") devices, such as a keyboard, a mouse, and a video display. The information handling system may also include one or more buses operable to transmit communication between the various hardware components.

For the purposes of this disclosure, computer-readable media may include any instrumentality or aggregation of instrumentalities that may retain data and/or instructions for a period of time. Computer-readable media may include, without limitation, storage media such as a direct access storage device (e.g., a hard disk drive or floppy disk), a sequential access storage device (e.g., a tape disk drive), compact disk, CD-ROM, DVD, random access memory (RAM), read-only memory (ROM), electrically erasable programmable read-only memory (EEPROM), and/or flash memory; as well as communications media such as wires, optical fibers, microwaves, radio waves, and other electromagnetic and/or optical carriers; and/or any combination of the foregoing.

For the purposes of this disclosure, information handling resources may broadly refer to any component system, device or apparatus of an information handling system, including without limitation processors, service processors, basic input/output systems (BIOSs), buses, memories, I/O devices and/or interfaces, storage resources, network interfaces, motherboards, and/or any other components and/or elements of an information handling system.

Figure 1:
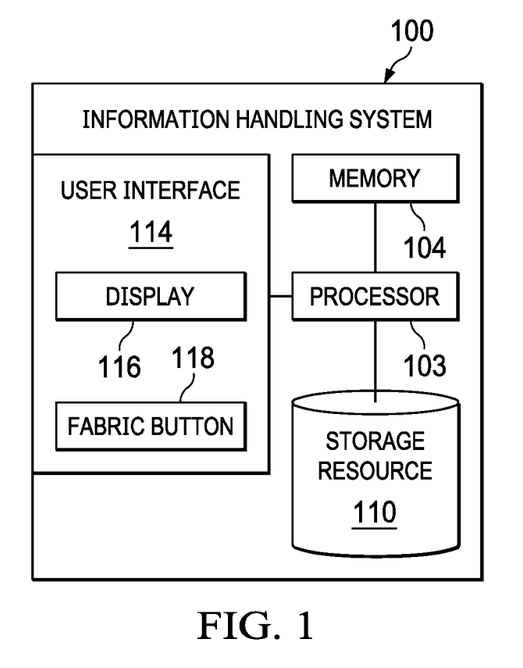
FIG. 1 illustrates a functional block diagram of selected components of an example information handling system, in accordance with embodiments of the present disclosure.

FIG. 1 illustrates a functional block diagram of selected components of an example information handling system 100, in accordance with embodiments of the present disclosure. In some embodiments, information handling system 100 may be a personal computer (e.g., a desktop computer or a portable computer). In other embodiments, information handling system 100 may comprise a mobile device (e.g., smart phone, a tablet computing device, a handheld computing device, a personal digital assistant, or any other device that may be readily transported on a person of a user of such mobile device).

As depicted in FIG. 1, information handling system 100 may include a processor 103, a memory 104 communicatively coupled to processor 103, a storage resource 110 communicatively coupled to processor 103, and a user interface 114 communicatively coupled to processor 103.

Processor 103 may include any system, device, or apparatus configured to interpret and/or execute program instructions and/or process data, and may include, without limitation, a microprocessor, microcontroller, digital signal processor (DSP), application specific integrated circuit (ASIC), or any other digital or analog circuitry configured to interpret and/or execute program instructions and/or process data. In some embodiments, processor 103 may interpret and/or execute program instructions and/or process data stored in memory 104, storage resource 110, and/or another component of information handling system 100.

Memory 104 may be communicatively coupled to processor 103 and may include any system, device, or apparatus configured to retain program instructions and/or data for a period of time (e.g., computer-readable media). Memory 104 may include random access memory (RAM), electrically erasable programmable read-only memory (EEPROM), a PCMCIA card, flash memory, magnetic storage, opto-magnetic storage, or any suitable selection and/or array of volatile or non-volatile memory that retains data after power to its associated information handling system 100 is turned off.

Storage resource 110 may include any system, device, or apparatus configured to store data. Storage resource 110 may include one or more hard disk drives, magnetic tape libraries, optical disk drives, magneto-optical disk drives, solid state storage drives, compact disk drives, compact disk arrays, disk array controllers, and/or any other systems, apparatuses or devices configured to store data. In certain embodiments, storage resource 110 may include one or more storage enclosures configured to hold and/or power one or more of such devices. In the embodiments represented by FIG. 1, storage resource 110 may reside within information handling system 100. However, in other embodiments, storage resource 110 may reside external to information handling system 100 (e.g., may be coupled to information handling system 100 via a network).

User interface 114 may comprise any instrumentality or aggregation of instrumentalities by which a user may interact with information handling system 100. For example, user interface 114 may permit a user to input data and/or instructions into information handling system 100 (e.g., via a keypad, keyboard, touch screen, microphone, camera, and/or other data input device), and/or otherwise manipulate information handling system 100 and its associated components. User interface 114 may also permit information handling system 100 to communicate data to a user (e.g., via a display device, speaker, and/or other data output device). As shown in FIG. 1, user interface 114 may include one or more of a display 116 and a fabric button 118.

Display 116 may comprise any suitable system, device, or apparatus configured to display human-perceptible graphical data and/or alphanumeric data to a user. For example, in some embodiments, display 116 may comprise a liquid crystal display.

Fabric button 118 may comprise any system, device, or apparatus constructed from an electrically-conductive fabric, which may sense a change in impedance or other electrical property of fabric button 118 in response to a mechanical force (e.g., a user's press) upon such fabric button.

In addition to processor 103, memory 104, storage resource 110, and user interface 114, information handling system 100 may include one or more other information handling resources. Such an information handling resource may include any component system, device or apparatus of an information handling system, including without limitation, a processor, bus, memory, I/O device and/or interface, storage resource (e.g., hard disk drives), network interface, electro-mechanical device (e.g., fan), display, power supply, and/or any portion thereof. An information handling resource may comprise any suitable package or form factor, including without limitation an integrated circuit package or a printed circuit board having mounted thereon one or more integrated circuits.

Figure 2A:
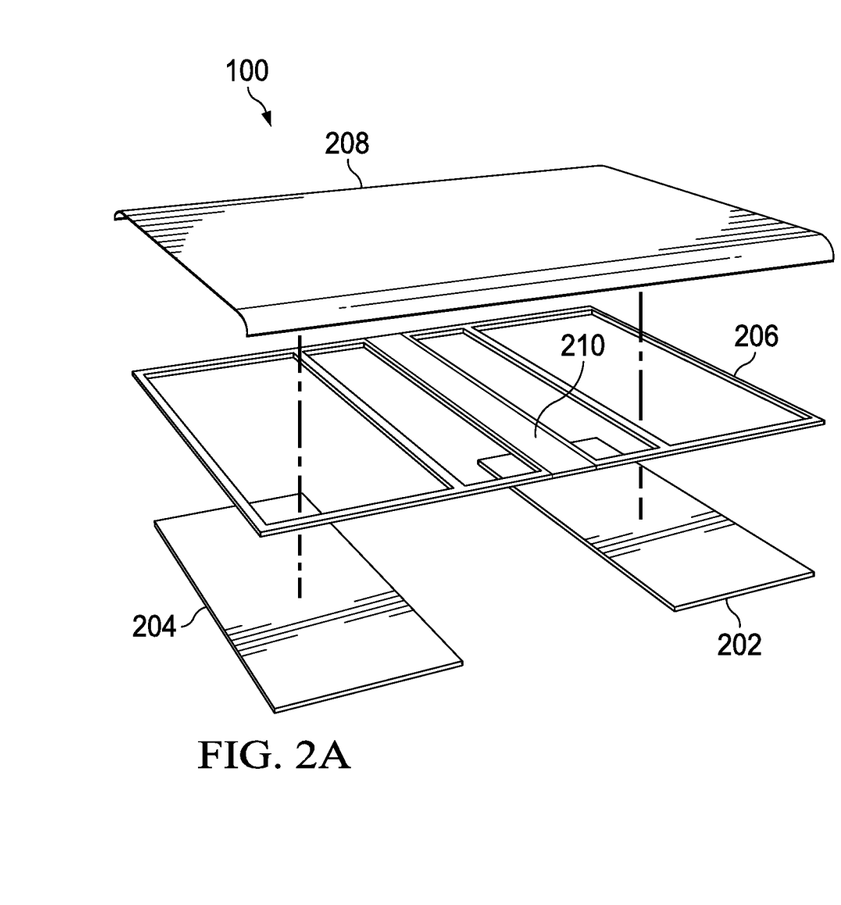
FIG. 2A illustrates an exploded perspective view of an example chassis for an information handling system, in accordance with embodiments of the present disclosure.
Figure 2B:
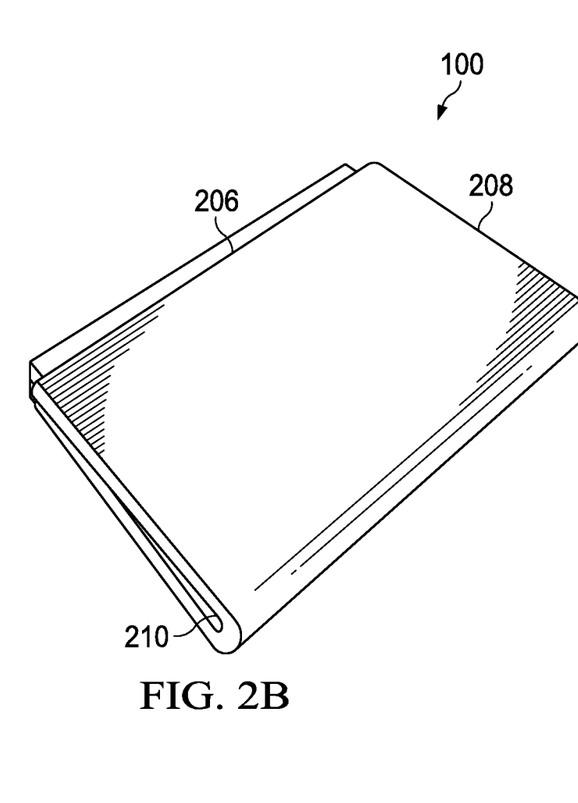
FIG. 2B illustrates an exterior assembled view of an example information handling system, in accordance with embodiments of the present disclosure.

FIG. 2A illustrates an exploded perspective view of selected components of an example chassis for information handling system 100 while FIG. 2B illustrates an exterior assembled view of information handling system 100, in accordance with embodiments of the present disclosure. As shown in FIGS. 2A and 2B, a chassis for information handling system 100 may include a display assembly 202, a keyboard assembly 204, a frame 206, and a fabric cover 208.

Each of display assembly 202 and keyboard assembly 204 may have an enclosure made from one or more suitable materials, including without limitation plastic, titanium, steel, and/or aluminum.

Frame 206 may be formed from one or more suitable materials, including without limitation plastic, titanium, steel, and/or aluminum. As shown in FIG. 2A, frame 206 may include a flexible portion 210 allowing frame to bend about flexible portion 210 such that flexible portion 210 acts as a hinge.

Fabric cover 208 may comprise any suitable fabric (e.g., nylon, carbon fiber, etc.).

The chassis of information handling system 100 may be assembled by tensioning fabric cover 208 over frame 206 and mechanically coupling each of display assembly 202 and keyboard assembly 204 to frame 206. Fabric cover 208 may be pliable, and because frame 206 includes flexible portion 210, a user may open and close display assembly 202 relative to keyboard assembly 204 as desired.

Figure 3A:
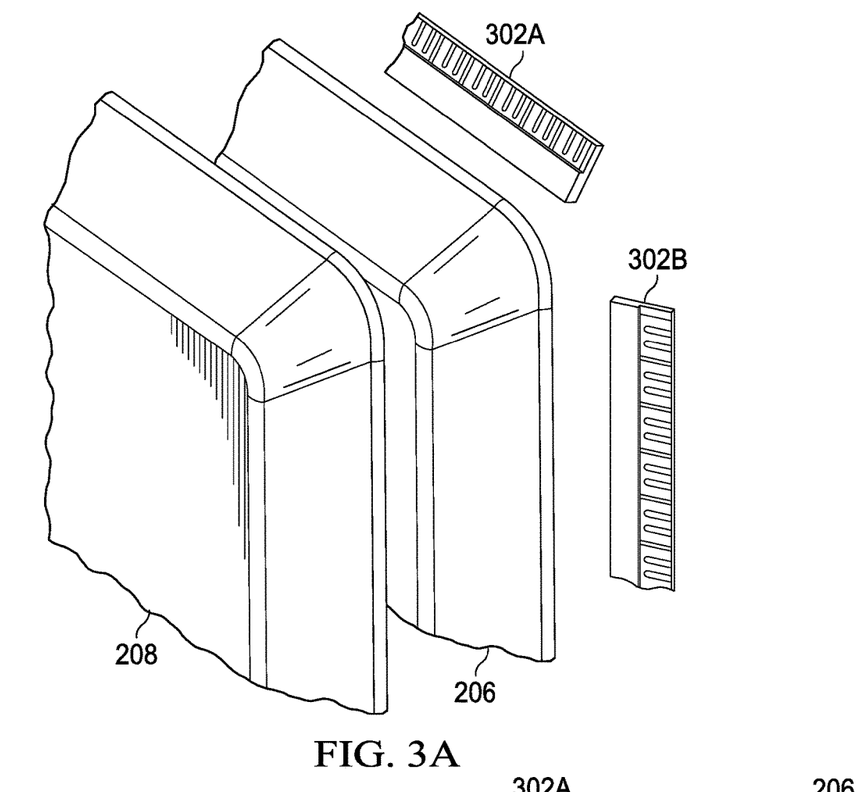
FIG. 3A illustrates an exploded perspective view of selected components of a portion of an example chassis for an information handling system, in accordance with embodiments of the present disclosure.
Figure 3B:
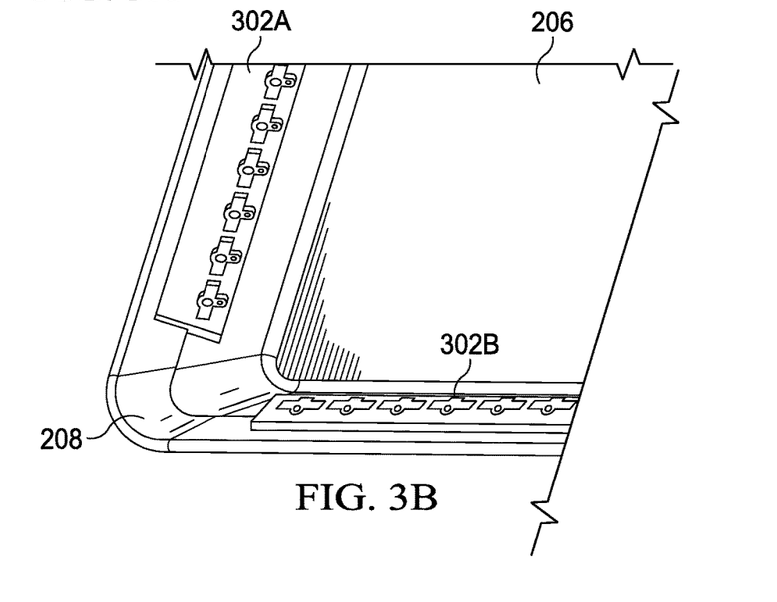
FIG. 3B illustrates an assembled view of the selected components shown in FIG. 3A, in accordance with embodiments of the present disclosure.

FIG. 3A illustrates an exploded perspective view of selected components of a portion of an example chassis for information handling system 100 while FIG. 3B illustrates an assembled view of the selected components shown in FIG. 3A, in accordance with embodiments of the present disclosure. As shown in FIGS. 3A and 3B, fabric cover 208 may be tensioned over and attached to frame 206. In addition, contact assemblies 302 may be mechanically coupled to frame 206 and fabric cover 208. As described in greater detail below, each contact assembly 302 may include one or more electrical contacts coupled to conductive fiber within fabric cover 208, and configured to sense interaction with a fabric button 118 (e.g., a force applied to a particular area of fabric cover 208). As shown in FIGS. 3A and 3B, contact assemblies 302 may include a row contact assembly 302A and a column contact assembly 302B. Accordingly, as described in greater detail below, contacts of row contact assembly 302A may determine a location of interaction in a first axis of the two-dimensional surface of fabric cover 208 while contacts of column contact assembly 302B may determine a location of interaction in a second axis (perpendicular to the first axis) of the two-dimensional surface of fabric cover 208. Thus, together, contacts of contact assemblies 302 may provide a coordinate location of a mechanical force interacting with fabric cover 208.

Figure 4:
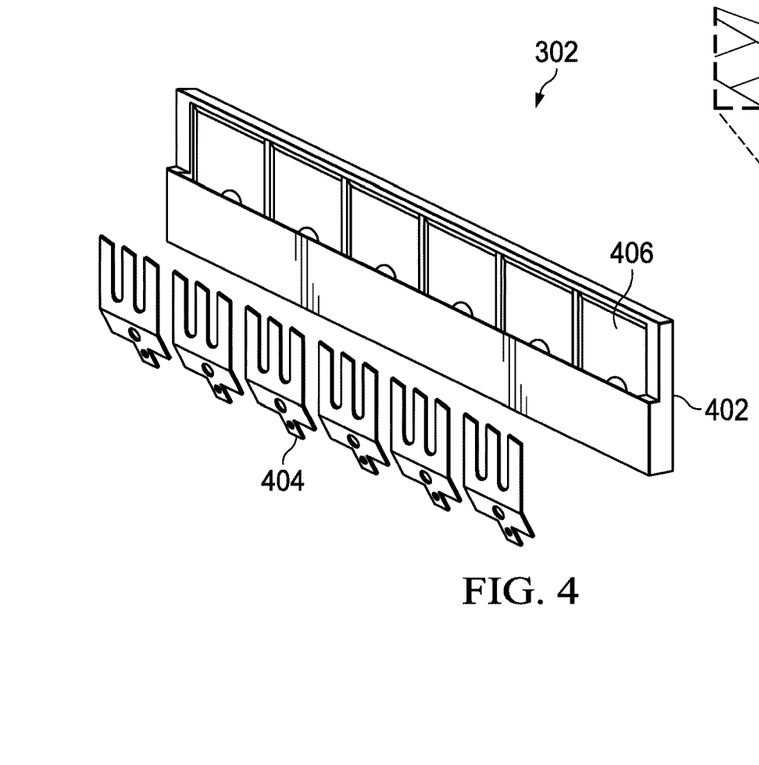
FIG. 4 illustrates an exploded perspective view of selected components of a contact assembly, in accordance with embodiments of the present disclosure.

FIG. 4 illustrates an exploded perspective view of selected components of a contact assembly 302, in accordance with embodiments of the present disclosure. As shown in FIG. 4, a contact assembly 302 may include a contact carrier 402 having a plurality of channels 406, each channel 406 configured to receive a corresponding electrical contact 404.

Figure 5:
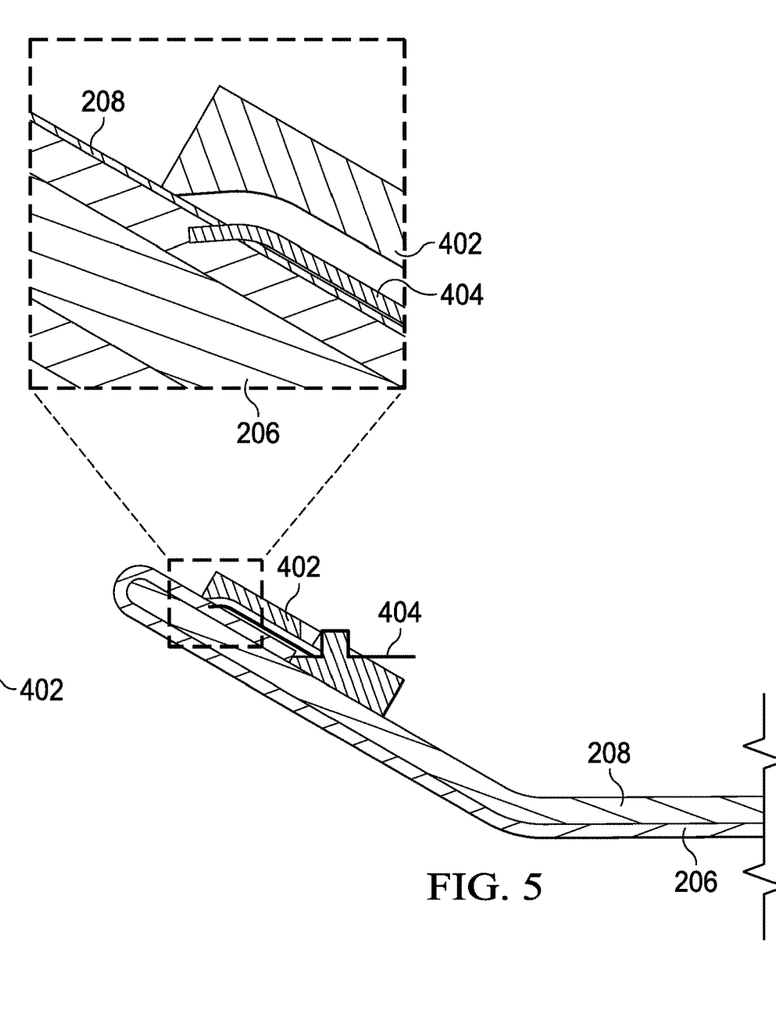
FIG. 5 illustrates a cross-sectional assembled view of selected components of an example chassis for an information handling system, in accordance with embodiments of the present disclosure.

FIG. 5 illustrates an cross-sectional assembled view of selected components of an example chassis for information handling system 100, in accordance with embodiments of the present disclosure. As shown in FIG. 5, contact assembly 302 may be assembled and mechanically coupled to frame 206 and fabric cover 208 such that each electrical contact 404 bites into fabric cover 208 and couples to a corresponding conductive fiber trace within fabric cover 208, thus allowing an electrical contact 404 to sense an interaction with the corresponding conductive fiber trace.

Figure 6:
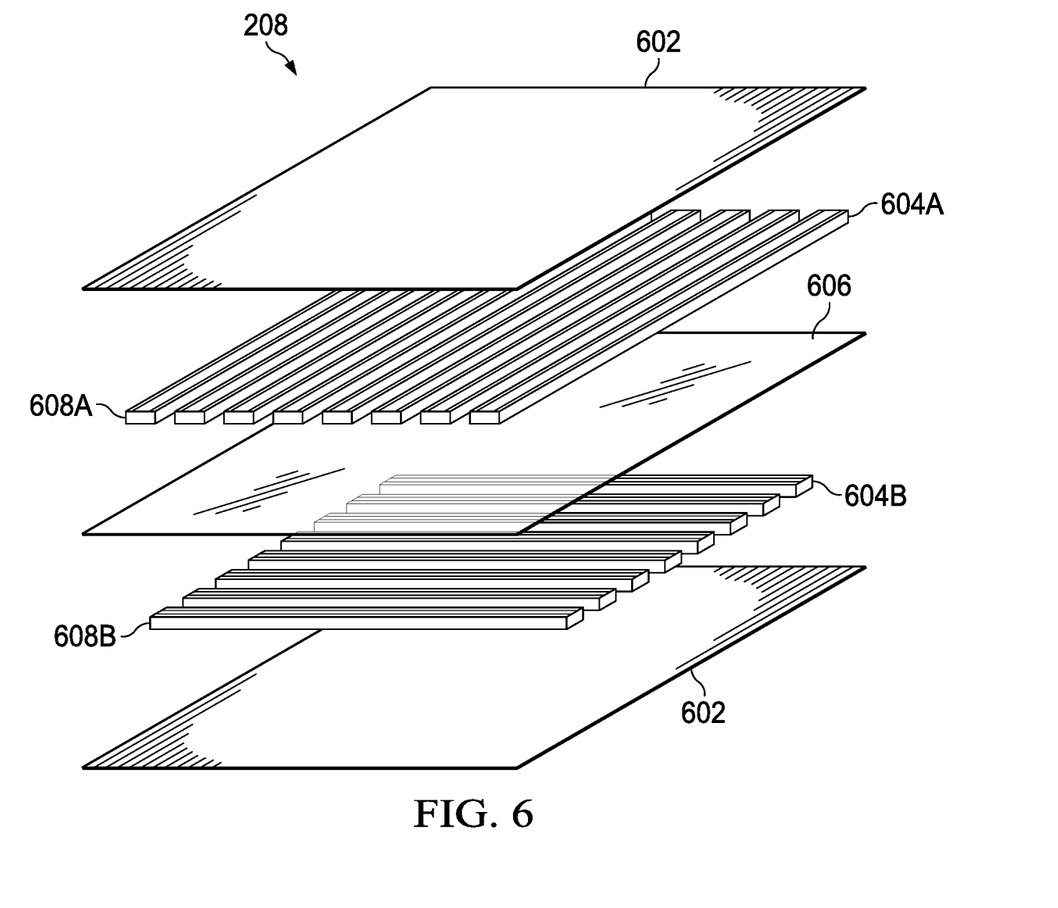
FIG. 6 illustrates an exploded perspective view of selected components of a fabric cover, in accordance with embodiments of the present disclosure.

FIG. 6 illustrates an exploded perspective view of selected components of fabric cover 208, in accordance with embodiments of the present disclosure. As shown in FIG. 6, fabric cover 208 may comprise a plurality of layers comprising a piezoresistive core layer 606 formed of piezoresistive material, a first conductive layer 604A of conductive fibers sandwiched between piezoresistive core layer 606 and a first non-conductive layer 602 of non-conductive fabric, and a second conductive layer 604B of conductive fibers sandwiched between piezoresistive core layer 606 and a second non-conductive layer 602 of non-conductive fabric. First conductive layer 604A may comprise a plurality of conductive fiber traces 608A, each of which may terminate at a corresponding electrical contact 404 of row contact assembly 302A. Similarly, second conductive layer 604B may comprise a plurality of conductive fiber traces 608B each of which may terminate at a corresponding electrical contact 404 of column contact assembly 302B.

In operation, when a force is applied to fabric cover 208 (e.g., in a direction perpendicular to its surface) such force may cause a localized decrease in impedance in piezoresistive core layer 606, which may be sensed by the conductive fiber traces 608A and 608B proximate to such localized decrease in impedance. By determining which two-dimensional row and column are associated with such conductive fiber traces 608A and 608B, a location of the force upon fabric cover 208 may be determined. Thus, fabric cover 208 may implement a fabric button 118 or a two-dimensional array of fabric buttons 118, thus providing a user interface on a surface of fabric cover 208.

In some embodiments, wherein only a determination of force applied in a one-dimensional axis is desired, fabric cover 208 may only include a single conductive layer 604.

Figure 7:
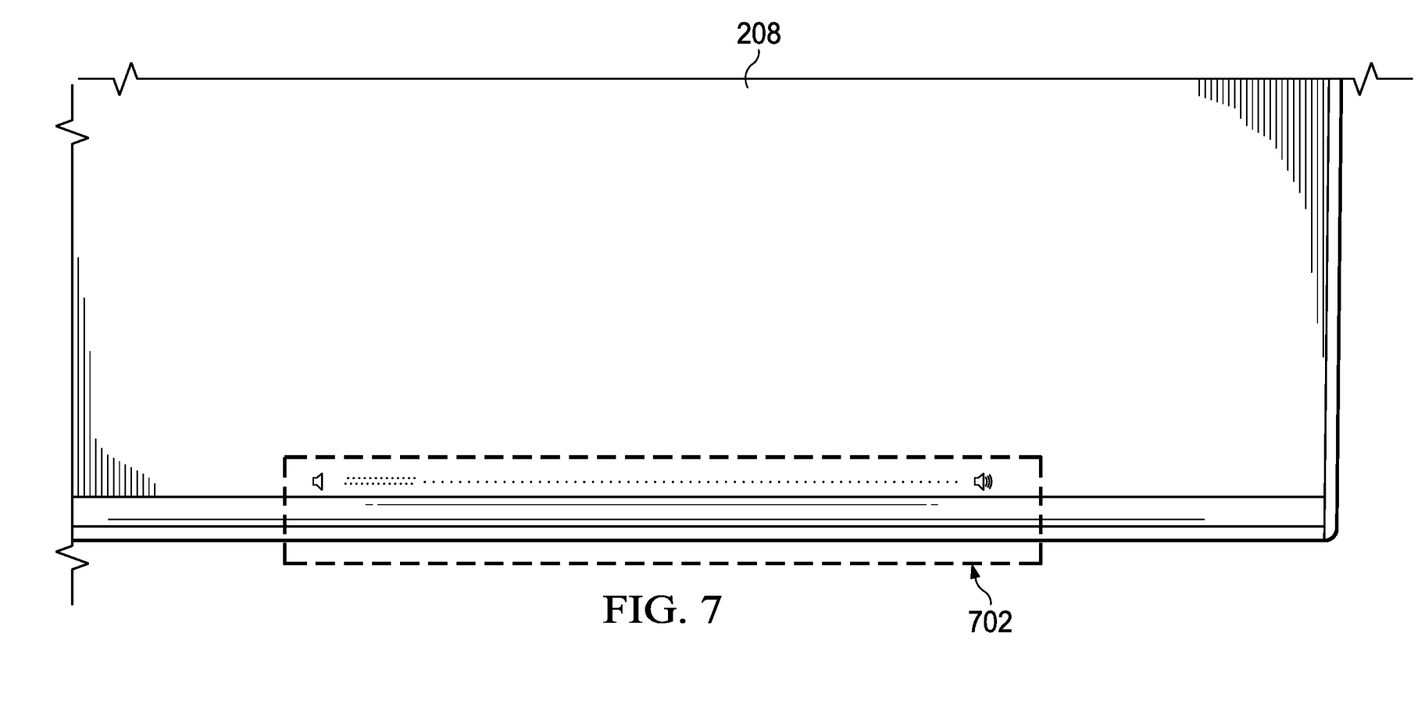
FIG. 7 illustrates an example fabric button, in accordance with embodiments of the present disclosure.

FIG. 7 depicts an example of such a fabric button 118, in accordance with embodiments of the present disclosure. As shown in FIG. 7, a portion 702 of fabric cover 208 may have printed or otherwise affixed thereto a visual indication of the presence of a fabric button 118 and in some instances a functionality of such fabric button 118. In the example shown in FIG. 7, a user may control a volume of sound reproduced from information handling system 100 by touching an appropriate area of portion 702 corresponding to the volume desired by the user.

In addition to sensing a force applied by a user to fabric cover 208, the systems and methods disclosed herein may also be used to detect other events for which a force or a change in force may be applied to fabric cover 208. For example, in some embodiments, a change in force in the area of the hinge of information handling system 100 may be used to determine whether or not display assembly 202 and keyboard assembly 204 are in an open or closed position relative to one another.

Figure 8:
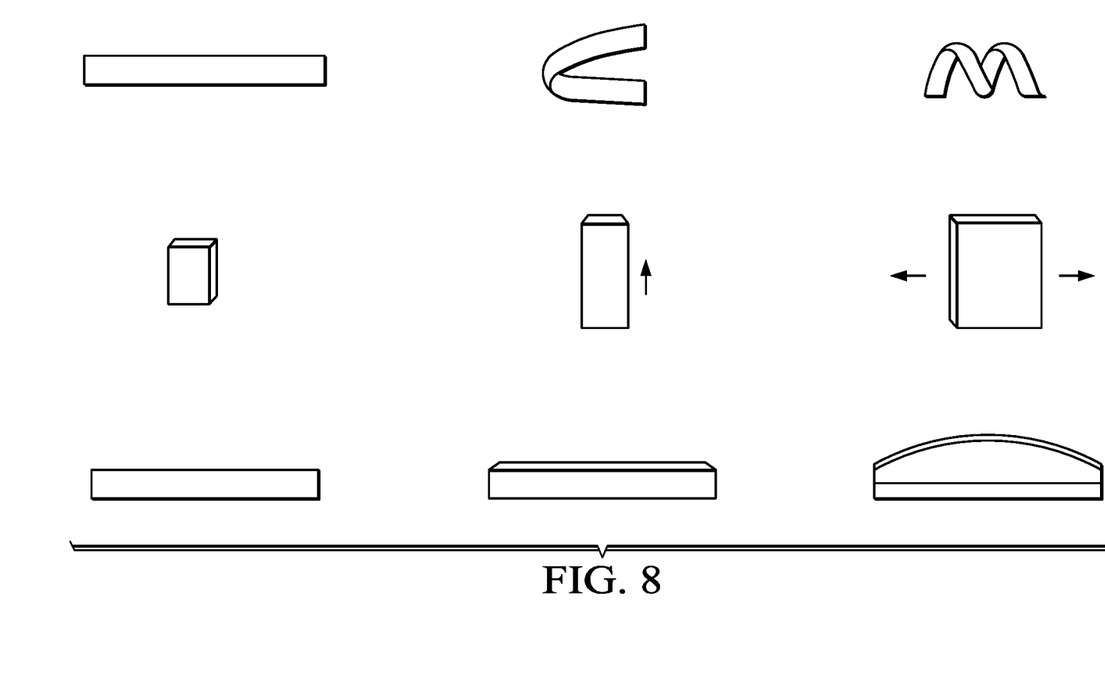
FIG. 8 illustrates a number of example shapes and microtextures that a fabric button may possess, in accordance with embodiments of the present disclosure.

Furthermore, use of a flexible fabric cover 208 may allow for a fabric button 118 to have a wide range of shapes and/or microtextures to allow for various different types of fabric buttons 118. To that end, FIG. 8 illustrates a number of example shapes and microtextures that a fabric button 118 or its components parts (e.g., piezoresistive core layer 606) may possess in order for such fabric button 118 to have a particular desired function.

As used herein, when two or more elements are referred to as "coupled" to one another, such term indicates that such two or more elements are in electronic communication or mechanical communication, as applicable, whether connected indirectly or directly, with or without intervening elements.

This disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Moreover, reference in the appended claims to an apparatus or system or a component of an apparatus or system being adapted to, arranged to, capable of, configured to, enabled to, operable to, or operative to perform a particular function encompasses that apparatus, system, or component, whether or not it or that particular function is activated, turned on, or unlocked, as long as that apparatus, system, or component is so adapted, arranged, capable, configured, enabled, operable, or operative. Accordingly, modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set.

Although exemplary embodiments are illustrated in the figures and described above, the principles of the present disclosure may be implemented using any number of techniques, whether currently known or not. The present disclosure should in no way be limited to the exemplary implementations and techniques illustrated in the figures and described above.

Unless otherwise specifically noted, articles depicted in the figures are not necessarily drawn to scale.

All examples and conditional language recited herein are intended for pedagogical objects to aid the reader in understanding the disclosure and the concepts contributed by the inventor to furthering the art, and are construed as being without limitation to such specifically recited examples and conditions. Although embodiments of the present disclosure have been described in detail, it should be understood that various changes, substitutions, and alterations could be made hereto without departing from the spirit and scope of the disclosure.

Although specific advantages have been enumerated above, various embodiments may include some, none, or all of the enumerated advantages. Additionally, other technical advantages may become readily apparent to one of ordinary skill in the art after review of the foregoing figures and description.

To aid the Patent Office and any readers of any patent issued on this application in interpreting the claims appended hereto, applicants wish to note that they do not intend any of the appended claims or claim elements to invoke 35 U.S.C. § 112(f) unless the words "means for" or "step for" are explicitly used in the particular claim.

What is claimed is:

1. A system comprising:
    a frame;
    a fabric cover mechanically coupled to and covering part of the frame, the fabric cover comprising a plurality of layers including:
        a first non-conductive fabric layer;
        a second non-conductive fabric layer;
        a piezoresistive core layer between the first non-conductive fabric layer and the second non-conductive fabric layer; and
        a first conductive layer comprising a plurality of first conductive fiber traces and located between the first non-conductive fabric layer and the second non-conductive fabric layer;

a first contact assembly mechanically coupled to the frame and comprising a plurality of first electrical contacts, each of the first electrical contacts electrically coupled to a corresponding one of the plurality of first conductive fiber traces; and a processing subsystem communicatively coupled to the first contact assembly and configured to determine a location of the fabric cover in which a localized impedance of the piezoresistive core layer indicates a mechanical force applied to the fabric cover proximate to such localized impedance.

2. The system of claim 1, further comprising:

a second conductive layer comprising a plurality of second conductive fiber traces located between the second non-conductive fabric layer and the piezoresistive core layer, wherein the first conductive layer is located between the first non-conductive fabric layer and the piezoresistive core layer; and a second contact assembly mechanically coupled to the frame and comprising a plurality of second electrical contacts, each of the second electrical contacts electrically coupled to a corresponding one of the plurality of second conductive fiber traces;

wherein the processing subsystem is further communicatively coupled to the second contact assembly and configured to determine a location of the fabric cover in which a localized impedance of the piezoresistive core layer indicates a mechanical force applied to the fabric cover proximate to such localized impedance.

3. The system of claim 1, wherein the mechanical force is that of a person applying the mechanical force to a surface of the fabric cover.

4. The system of claim 1, further comprising:

a first mechanical member mechanically coupled to the frame; and a second mechanical member mechanically coupled to the frame;

wherein the frame comprises a flexible portion to allow the second mechanical member to be movable relative to the first mechanical member between a closed position and at least one open position.

5. The system of claim 4, wherein the mechanical force is that of the second mechanical member moving relative to the first mechanical member from the closed position and the at least one open position or vice versa.

6. The system of claim 4, wherein the first mechanical member comprises a keyboard assembly.

7. The system of claim 4, wherein the second mechanical member comprises a display assembly.

8. The system of claim 1, wherein the fabric cover includes at least one of a shape or a microtexture adapted to a particular functionality of a fabric button implemented by the fabric cover.

9. A fabric cover configured to mechanically couple to and cover part of a frame, the fabric cover comprising a plurality of layers including:

a first non-conductive fabric layer;

a second non-conductive fabric layer;

a piezoresistive core layer between the first non-conductive fabric layer and the second fabric non-conductive layer; and a first conductive layer comprising a plurality of first conductive fiber traces and located between the first non-conductive fabric layer and the second non-conductive fabric layer;

wherein:

a localized impedance of the piezoresistive core layer indicates a mechanical force applied to the fabric cover proximate to such localized impedance; and the fabric cover includes at least one of a shape or a microtexture adapted to a particular functionality of a fabric button implemented by the fabric cover.

10. The fabric cover of claim 9, further comprising:

a second conductive layer comprising a plurality of second conductive fiber traces located between the second non-conductive fabric layer and the piezoresistive core layer, wherein the first conductive layer is located between the first non-conductive fabric layer and piezoresistive core layer.

11. The fabric cover of claim 9, wherein the mechanical force is that of a person applying the mechanical force to a surface of the fabric cover.

12. A method comprising:

coupling a fabric cover to a frame to cover the frame, the fabric cover comprising a plurality of layers including:

a first non-conductive fabric layer;

a second non-conductive fabric layer;

a piezoresistive core layer between the first non-conductive fabric layer and the second non-conductive fabric layer; and a first conductive layer comprising a plurality of first conductive fiber traces and located between the first non-conductive fabric layer and the second non-conductive fabric layer;

mechanically coupling a first contact assembly mechanically to the frame, the first contact assembly comprising a plurality of first electrical contacts, each of the first electrical contacts electrically coupled to a corresponding one of the plurality of first conductive fiber traces; and communicatively coupling a processing subsystem to the first contact assembly, the processing subsystem configured to determine a location of the fabric cover in which a localized impedance of the piezoresistive core layer indicates a mechanical force applied to the fabric cover proximate to such localized impedance.

13. The method of claim 12, wherein:

the fabric cover comprises a plurality of second conductive fiber traces located between the second non-conductive fabric layer and the piezoresistive core layer, further wherein the first conductive layer is located between the first non-conductive fabric layer and the piezoresistive core layer;

the method further comprising:

mechanically coupling a second contact assembly to the frame, the second contact assembly comprising a plurality of second electrical contacts, each of the second electrical contacts electrically coupled to a corresponding one of the plurality of second conductive fiber traces; and communicatively coupling the processing subsystem to the second contact assembly.

14. The method of claim 12, wherein the mechanical force is that of a person applying the mechanical force to a surface of the fabric cover.

15. The method of claim 12, further comprising:

mechanically coupling a first mechanical member to the frame; and mechanically coupling a second mechanical member to the frame;

wherein the frame comprises a flexible portion to allow the second mechanical member to be movable relative to the first mechanical member between a closed position and at least one open position.

16. The method of claim 15, wherein the mechanical force is that of the second mechanical member moving relative to the first mechanical member from the closed position and the at least one open position or vice versa.

17. The method of claim 15, wherein the first mechanical member comprises a keyboard assembly.

18. The method of claim 15, wherein the second mechanical member comprises a display assembly.

19. The method of claim 12, further comprising forming within the fabric cover at least one of a shape or a microtexture adapted to a particular functionality of a fabric button implemented by the fabric cover.

* * * * *